US008379199B2

(12) United States Patent
Freese et al.

(10) Patent No.: US 8,379,199 B2
(45) Date of Patent: Feb. 19, 2013

(54) SELF-CONTAINED MULTIVARIATE OPTICAL COMPUTING AND ANALYSIS SYSTEM

(75) Inventors: Robert P. Freese, Youngsville, NC (US); Terrell K. Teague, Walworth, NY (US); David L. Perkins, Irmo, SC (US); William J. Soltmann, Columbia, SC (US)

(73) Assignee: Halliburton Energy Services, Inc., Houston, TX (US)

( * ) Notice: Subject to any disclaimer, the term of this patent is extended or adjusted under 35 U.S.C. 154(b) by 635 days.

(21) Appl. No.: 12/513,265

(22) PCT Filed: Nov. 1, 2007

(86) PCT No.: PCT/US2007/083280
§ 371 (c)(1),
(2), (4) Date: Mar. 26, 2010

(87) PCT Pub. No.: WO2008/057905
PCT Pub. Date: May 15, 2008

(65) Prior Publication Data
US 2010/0182600 A1 Jul. 22, 2010

Related U.S. Application Data

(60) Provisional application No. 60/864,047, filed on Nov. 2, 2006, provisional application No. 60/891,826, filed on Feb. 27, 2007.

(51) Int. Cl.
*G01J 3/40* (2006.01)
(52) U.S. Cl. .......................... 356/303; 356/300
(58) Field of Classification Search .............. 356/300, 356/303, 417, 37, 318; 250/341.8
See application file for complete search history.

(56) References Cited

U.S. PATENT DOCUMENTS

| | | |
|---|---|---|
| 5,090,807 A | 2/1992 | Tai |
| 5,737,076 A | 4/1998 | Glaus et al. |
| 5,945,676 A | 8/1999 | Khalil et al. |
| 6,198,531 B1 | 3/2001 | Myrick et al. |
| 6,430,513 B1 | 8/2002 | Wang et al. |
| 6,529,276 B1 | 3/2003 | Myrick |
| 6,600,560 B2 | 7/2003 | Mikkelsen et al. |
| 6,741,335 B2 | 5/2004 | Kinrot et al. |
| 6,870,629 B1 | 3/2005 | Vogel et al. |
| 6,995,840 B2 | 2/2006 | Hagler |
| 7,123,844 B2 | 10/2006 | Myrick |
| 7,138,156 B1 | 11/2006 | Myrick et al. |
| 7,245,374 B2 | 7/2007 | Hendriks |
| 7,399,968 B2 | 7/2008 | Lewis et al. |
| 7,405,825 B2 | 7/2008 | Schuurmans et al. |

(Continued)

FOREIGN PATENT DOCUMENTS

| | | |
|---|---|---|
| WO | 2004/057284 A1 | 7/2004 |
| WO | 2005/062986 A2 | 7/2005 |

(Continued)

*Primary Examiner* — Layla Lauchman

(57) ABSTRACT

An optical analysis system for measuring compositions of a sample includes a light source radiating a first light. A modulator disposed in a ray path of the light modulates the light to a desired frequency. A spectral element filters the light for a spectral range of interest of the sample. An optical filter receives a first light beam split from the light reflecting from the sample and optically filters data carried by the first light beam into at least one orthogonal component of the first light beam. A first detector measures a property of the orthogonal component. A second detector receives a second light beam split from the light reflecting from the sample for comparison of the property of the orthogonal component to the second light beam. An accelerometer senses when to acquire data from the sample.

28 Claims, 10 Drawing Sheets

U.S. PATENT DOCUMENTS

| | | |
|---|---|---|
| 7,623,233 B2 | 11/2009 | Freese et al. |
| 7,671,973 B2 | 3/2010 | Van Beek et al. |
| 8,154,726 B2 * | 4/2012 | Blackburn et al. ............ 356/416 |
| 2003/0117628 A1 | 6/2003 | Harju et al. |
| 2006/0142955 A1 | 6/2006 | Jones et al. |
| 2006/0158734 A1 | 7/2006 | Schuurmans et al. |
| 2008/0231849 A1 | 9/2008 | Myrick et al. |
| 2008/0309930 A1 | 12/2008 | Rensen |
| 2009/0002697 A1 | 1/2009 | Freese et al. |
| 2009/0015819 A1 | 1/2009 | Van Beek et al. |
| 2009/0033933 A1 | 2/2009 | Myrick |
| 2009/0097024 A1 | 4/2009 | Blackburn et al. |
| 2009/0299946 A1 * | 12/2009 | Myrick et al. .................. 706/52 |
| 2010/0042348 A1 | 2/2010 | Bakker |

FOREIGN PATENT DOCUMENTS

| | | |
|---|---|---|
| WO | 2007/062202 A1 | 5/2007 |
| WO | 2007061435 A1 | 5/2007 |
| WO | 2007061436 A1 | 5/2007 |
| WO | 2007061437 A1 | 5/2007 |
| WO | 2007062224 A1 | 5/2007 |
| WO | 2007064578 A1 | 6/2007 |
| WO | 2008002903 A2 | 1/2008 |
| WO | 2008057912 A2 | 5/2008 |
| WO | 2008057913 A2 | 5/2008 |
| WO | 2008121684 | 10/2008 |

* cited by examiner

SELF-CONTAINED MULTIVARIATE OPTICAL COMPUTING AND ANALYSIS SYSTEM

CROSS-REFERENCE TO RELATED APPLICATIONS

This application claims benefit of U.S. Provisional Application Ser. No. 60/864,047, filed on Nov. 2, 2006, and U.S. Provisional Application Ser. No. 60/891,826, filed on Feb. 27, 2007.

FIELD OF THE DISCLOSURE

The present disclosure relates to spectroscopy analysis systems. More particularly, the disclosure relates to a multivariate optical computing and analysis system, which is self-contained and capable of remote operation and control.

BACKGROUND OF THE DISCLOSURE

Light conveys information through data. When light interacts with matter, for example, it carries away information about the physical and chemical properties of the matter. A property of the light, for example, its intensity, may be measured and interpreted to provide information about the matter with which it interacted. That is, the data carried by the light through its intensity may be measured to derive information about the matter. Similarly, in optical communications systems, light data is manipulated to convey information over an optical transmission medium, for example fiber optic cable. The data is measured when the light signal is received to derive information.

In general, a simple measurement of light intensity is difficult to convert to information because it likely contains interfering data. That is, several factors may contribute to the intensity of light, even in a relatively restricted wavelength range. It is often impossible to adequately measure the data relating to one of these factors since the contribution of the other factors is unknown.

It is possible, however, to derive information from light. An estimate may be obtained, for example, by separating light from several samples into wavelength bands and performing a multiple linear regression of the intensity of these bands against the results of conventional measurements of the desired information for each sample. For example, a polymer sample may be illuminated so that light from the polymer carries information such as the sample's ethylene content. Light from each of several samples may be directed to a series of bandpass filters which separate predetermined wavelength bands from the light. Light detectors following the bandpass filters measure the intensity of each light band. If the ethylene content of each polymer sample is measured using conventional means, a multiple linear regression of ten measured bandpass intensities against the measured ethylene content for each sample may produce an equation such as:

$$y = a_0 + a_1 w_1 + a_2 w_2 + \ldots + a_{10} w_{10} \quad \text{(``Equation 1'')}$$

where y is ethylene content, $a_n$ are constants determined by the regression analysis, and $w_n$ is light intensity for each wavelength band.

Equation 1 may be used to estimate ethylene content of subsequent samples of the same polymer type. Depending on the circumstances, however, the estimate may be unacceptably inaccurate since factors other than ethylene may affect the intensity of the wavelength bands. These other factors may not change from one sample to the next in a manner consistent with ethylene.

A more accurate estimate may be obtained by compressing the data carried by the light into principal components. To obtain the principal components, spectroscopic data is collected for a variety of samples of the same type of light, for example from illuminated samples of the same type of polymer. For example, the light samples may be spread into their wavelength spectra by a spectrograph so that the magnitude of each light sample at each wavelength may be measured. This data is then pooled and subjected to a linear-algebraic process known as singular value decomposition (SVD). SVD is at the heart of principal component analysis, which should be well understood in this art. Briefly, principal component analysis is a dimension reduction technique, which takes m spectra with n independent variables and constructs a new set of eigenvectors that are linear combinations of the original variables. The eigenvectors may be considered a new set of plotting axes. The primary axis, termed the first principal component, is the vector, which describes most of the data variability. Subsequent principal components describe successively less sample variability, until only noise is described by the higher order principal components.

Typically, the principal components are determined as normalized vectors. Thus, each component of a light sample may be expressed as $x_n z_n$, where $x_n$ is a scalar multiplier and $z_n$ is the normalized component vector for the $n_{th}$ component. That is, $z_n$ is a vector in a multi-dimensional space where each wavelength is a dimension. As should be well understood, normalization determines values for a component at each wavelength so that the component maintains it shape and so that the length of the principal component vector is equal to one. Thus, each normalized component vector has a shape and a magnitude so that the components may be used as the basic building blocks of all light samples having those principal components. Accordingly, each light sample may be described in the following format by the combination of the normalized principal components multiplied by the appropriate scalar multipliers:

$$x_1 z_1 + x_2 z_2 + \ldots + x_n z_n.$$

The scalar multipliers $x_n$ may be considered the "magnitudes" of the principal components in a given light sample when the principal components are understood to have a standardized magnitude as provided by normalization.

Because the principal components are orthogonal, they may be used in a relatively straightforward mathematical procedure to decompose a light sample into the component magnitudes, which accurately describe the data in the original sample. Since the original light sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. This is analogous to breaking a vector in a three dimensional Cartesian space into its X, Y and Z components. The dot product of the three-dimensional vector with each axis vector, assuming each axis vector has a magnitude of 1, gives the magnitude of the three dimensional vector in each of the three directions. The dot product of the original signal and some other vector that is not perpendicular to the other three dimensions provides redundant data, since this magnitude is already contributed by two or more of the orthogonal axes.

Because the principal components are orthogonal, or perpendicular, to each other, the dot, or direct, product of any principal component with any other principal component is zero. Physically, this means that the components do not interfere with each other. If data is altered to change the magnitude of one component in the original light signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the light samples. Thus, in a mathematical sense, the principal components are components of the original light that do not interfere with each other and that represent the most compact description of the entire data carried by the light. Physically, each principal component is a light signal that forms a part of the original light signal. Each has a shape over some wavelength range within the original wavelength range. Summing the principal components produces the original signal, provided each component has the proper magnitude.

The principal components comprise a compression of the data carried by the total light signal. In a physical sense, the shape and wavelength range of the principal components describe what data is in the total light signal while the magnitude of each component describes how much of that data is there. If several light samples contain the same types of data, but in differing amounts, then a single set of principal components may be used to exactly describe (except for noise) each light sample by applying appropriate magnitudes to the components.

The principal components may be used to accurately estimate information carried by the light. For example, suppose samples of a certain brand of gasoline, when illuminated, produce light having the same principal components. Spreading each light sample with a spectrograph may produce wavelength spectra having shapes that vary from one gasoline sample to another. The differences may be due to any of several factors, for example differences in octane rating or lead content.

The differences in the sample spectra may be described as differences in the magnitudes of the principal components. For example, the gasoline samples might have four principal components. The magnitudes $x_n$ of these components in one sample might be J, K, L, and M, whereas in the next sample the magnitudes may be 0.94 J, 1.07K, 1.13 L and 0.86M. As noted above, once the principal components are determined, these magnitudes exactly describe their respective light samples.

Refineries desiring to periodically measure octane rating in their product may derive the octane information from the component magnitudes. Octane rating may be dependent upon data in more than one of the components. Octane rating may also be determined through conventional chemical analysis. Thus, if the component magnitudes and octane rating for each of several gasoline samples are measured, a multiple linear regression analysis may be performed for the component magnitudes against octane rating to provide an equation such as:

$$y=a_0+a_1x_1+a_2x_2+a_3x_3+a_4x_4 \quad \text{(``Equation 2'')}$$

where y is octane rating, $a_n$ are constants determined by the regression analysis, and $x_1$, $x_2$, $x_3$ and $x_4$ are the first, second, third and fourth principal component magnitudes, respectively.

Using Equation 2, which may be referred to as a regression vector, refineries may accurately estimate octane rating of subsequent gasoline samples. Conventional systems perform regression vector calculations by computer, based on spectrograph measurements of the light sample by wavelength. The spectrograph system spreads the light sample into its spectrum and measures the intensity of the light at each wavelength over the spectrum wavelength range. If the regression vector in the Equation 2 form is used, the computer reads the intensity data and decomposes the light sample into the principal component magnitudes $x_n$ by determining the dot product of the total signal with each component. The component magnitudes are then applied to the regression equation to determine octane rating.

To simplify the procedure, however, the regression vector is typically converted to a form that is a function of wavelength so that only one dot product is performed. Each normalized principal component vector $z_n$ has a value over all or part of the total wavelength range. If each wavelength value of each component vector is multiplied by the regression constant $a_n$ corresponding to the component vector, and if the resulting weighted principal components are summed by wavelength, the regression vector takes the following form:

$$y=a_0+b_1u_1+b_2u_2+\ldots+b_nu_n \quad \text{(``Equation 3'')}$$

where y is octane rating, $a_0$ is the first regression constant from Equation 2, $b_n$ is the sum of the multiple of each regression constant $a_n$ from Equation 2 and the value of its respective normalized regression vector at wavelength n, and $u_n$ is the intensity of the light sample at wavelength n. Thus, the new constants define a vector in wavelength space that directly describes octane rating. The regression vector in a form as in Equation 3 represents the dot product of a light sample with this vector.

Normalization of the principal components provides the components with an arbitrary value for use during the regression analysis. Accordingly, it is very unlikely that the dot product result produced by the regression vector will be equal to the actual octane rating. The number will, however, be proportional to the octane rating. The proportionality factor may be determined by measuring octane rating of one or more samples by conventional means and comparing the result to the number produced by the regression vector. Thereafter, the computer can simply scale the dot product of the regression vector and spectrum to produce a number approximately equal to the octane rating.

In a conventional spectroscopy analysis system, a laser directs light to a sample by a bandpass filter, a beam splitter, a lens and a fiber optic cable. Light is reflected back through the cable and the beam splitter to another lens to a spectrograph. The spectrograph separates light from the illuminated sample by wavelength so that a detection device such as a charge couple detector can measure the intensity of the light at each wavelength. The charge couple detector is controlled by controller and cooled by a cooler. The detection device measures the light intensity of light from the spectrograph at each wavelength and outputs this data digitally to a computer, which stores the light intensity over the wavelength range. The computer also stores a previously derived regression vector for the desired sample property, for example octane, and sums the multiple of the light intensity and the regression vector intensity at each wavelength over the sampled wavelength range, thereby obtaining the dot product of the light from the substance and the regression vector. Since this number is proportional to octane rating, the octane rating of the sample is identified.

Since the spectrograph separates the sample light into its wavelengths, a detector is needed that can detect and distinguish the relatively small amounts of light at each wavelength. Charge couple devices provide high sensitivity throughout the visible spectral region and into the near infrared with extremely low noise. These devices also provide high quantum efficiency, long lifetime, imaging capability and solid-state characteristics. Unfortunately, however, charge couple devices and their required operational instrumentation are very expensive. Furthermore, the devices are sensitive to environmental conditions. In a refinery, for example, they must be protected from explosion, vibration and temperature fluctuations and are often placed in protective housings approximately the size of a refrigerator. The power requirements, cooling requirements, cost, complexity and maintenance requirements of these systems have made them impractical in many applications.

Multivariate optical computing (MOC) is a powerful predictive spectroscopic technique that incorporates a multi-wavelength spectral weighting directly into analytical instrumentation. This is in contrast to traditional data collection routines where digitized spectral data is post processed with a computer to correlate spectral signal with analyte concentration. Previous work has focused on performing such spectral weightings by employing interference filters called Multivariate Optical Elements (MOEs). Other researchers have realized comparable results by controlling the staring or integration time for each wavelength during the data collection process. All-optical computing methods have been shown to produce similar multivariate calibration models, but the measurement precision via an optical computation is superior to a traditional digital regression.

MOC has been demonstrated to simplify the instrumentation and data analysis requirements of a traditional multivariate calibration. Specifically, the MOE utilizes a thin film interference filter to sense the magnitude of a spectral pattern. A no-moving parts spectrometer highly selective to a particular analyte may be constructed by designing simple calculations based on the filter transmission and reflection spectra. Other research groups have also performed optical computations through the use of weighted integration intervals and acousto-optical tunable filters digital mirror arrays and holographic gratings.

The measurement precision of digital regression has been compared to various optical computing techniques including MOEs, positive/negative interference filters and weighted-integration scanning optical computing. In a high signal condition where the noise of the instrument is limited by photon counting, optical computing offers a higher measurement precision when compared to its digital regression counterpart. The enhancement in measurement precision for scanning instruments is related to the fraction of the total experiment time spent on the most important wavelengths. While the detector integrates or coadds measurements at these important wavelengths, the signal increases linearly while the noise increases as a square root of the signal. Another contribution to this measurement precision enhancement is a combination of the Felgott's and Jacquinot's advantage, which is possessed by MOE optical computing.

While various methodologies have been developed to enhance measurement accuracy in Optical Analysis Systems, no design has emerged that generally encompasses all of the desired characteristics as hereafter presented in accordance with the subject technology.

BRIEF SUMMARY OF THE DISCLOSURE

The present disclosure is directed generally to an optical system for multivariate optical computing in real-time. Multivariate optical computing (MOC) is generally described in U.S. Pat. No. 6,198,531 B1 to Myrick et al. and in U.S. Pat. No. 6,529,276 B1 to Myrick as a predictive spectroscopy technique that incorporates a multi-wavelength spectral weighting directly into analytical instrumentation. Both of these patents are incorporated herein for all purposes by reference thereto.

Since multivariate optical element (MOE)-based MOC uses detectors that see all wavelengths emanating from an illumination source simultaneously—including wavelengths that carry no information—measurement noise is reduced and measurement precision is increased in the system of the present disclosure by making the system sensitive primarily to wavelengths carrying information. Additionally, the present disclosure controls a spectral range of the illumination source by using bandpass filters or spectral elements having predetermined transmission characteristics. Further, in some aspect of the present disclosure, the system shines a light signal directly onto a sample and eliminates the use of, for instance, a fiber optic probe; therefore, the component parts of the disclosure are simple and economical to manufacture, assemble and use, with improved signal when the attenuation typical of a fiber optic probe is removed. These and other aspects and advantages of the present disclosure will be apparent from the following description and the attached drawings, or can be learned through practice of the disclosure.

According to one embodiment of the present disclosure, an optical analysis system generally includes an illumination source for shining light or other radiative energy through a set of lenses. Light levels are maximized through the optical system to enhance transmission (reduce loss) of the light. The illumination source subsequently shines the light through a multi-window (e.g., 10-window) chopper wheel. The chopper wheel rotates, for instance, at 40 Hertz (Hz), which produces a light beam modulated at 400 Hz. A modulated light signal is beneficial for reliable performance of the photodetectors in the system. The light beam passes through one or more spectral elements or filters, which control the spectral region of the light, which passes through them (and onto a sample). The light is reflected by a turning mirror down the center of the sampling tube and focused by a lens on the sample. Light is reflected back by the sample through the lens and back down the sampling tube, past the turning mirror. The light passes through a beam splitter with reflects part of the light ("signal A") through a multivariate optical element (MOE) and lens and onto a photodetector. Another part of the light ("signal B") passes through a lens onto another photodetector and acts as a reference signal. The system measures signal A and signal B, and a ratio of the two signals can be used to measure a concentration of the sample, e.g., a chemical of interest. Additionally, monitoring of signal A and/or signal B independently, or in some combination, can provide other information, such as powder segregation, packing of materials, effect of particle size. More specifically, any algebraic combination of signals A and B can be used according to the disclosure; e.g., A and/or B independently; A divided by B; A plus B; A minus B; B divided by A; B minus A, etcetera. For example, a ratio of signal A to signal B can provide a chemical measurement; individually, A signal and/or B signal can provide other homogeneity measures including physical make-up of the sample, packing, particle size, and/or separate physical and chemical properties.

According to another aspect of the disclosure, a method of determining information carried by light includes the steps of providing an optical analysis system having a multivariate optical element disposed to receive a source light from an illumination source; filtering the source light through a spectral element in the optical element analysis system; reflecting the filtered light through an inner region of a cavity in a first direction of a sample to be measured, the cavity defining a second region disposed about the inner region; focusing the reflected light proximate the sample; reflecting the focused light from the sample through the second region in a second direction of a beamsplitter, the light being reflected from the sample carrying data from the sample; splitting the sample carrying light with the beamsplitter into a first light and a second light; optically filtering the data of the first light with the multivariate optical element into an orthogonal component; directing the first light filtered by the multivariate optical element onto a first photodetector; directing the second light onto a second photodetector; and comparing the orthogonal component to information present in the second light to determine a property of the sample. In this aspect, the light is focused on, in or near the sample, the light having a focal point proximate the sample. Also in this aspect, the beamsplitter is a 50/50 beamsplitter.

The method in this aspect may also include the step of modulating the light from about 50 Hz to about 5000 Hz before filtering the light through the spectral element. A further step may include controlling a spectral range of the light source, the spectral element having a predetermined transmission characteristic for controlling the spectral range. Also in this aspect, the spectral element can be two or more spectral elements for controlling the spectral range of the light source.

Further, in this aspect of the disclosure, the method may include measuring a concentration of the sample ratio using a ratio of the first light and the second light. Additional steps may include monitoring the first light, the second light or combinations thereof to assess particle segregation of the sample; monitoring the first light, the second light or combinations thereof to assess density of the sample; monitoring the first light, the second light or combinations thereof to assess affect of particle size in the sample; monitoring the first light, the second light or combinations thereof to measure a chemical in the sample; monitoring the first light, the second light or combinations thereof to measure homogeneity of the sample and combinations of the foregoing steps.

Also in this aspect of the disclosure, the method can include the step of using a fiber optic probe. Moreover, the method may include preparing a chemometric model to make a similar measurement of the light reflected from the sample as a measurement made by the optical analysis system.

Another step may be using the illumination light from the outer annular region with the filtered light through the inner region of the cavity to determine the property of the sample.

In yet another aspect of the disclosure, an optical analysis system can be configured in a transmission mode rather than a reflectance mode as in the foregoing embodiments. In the transmission mode, light would pass through a sample (e.g., a fluid sample) and be collected on a far side of the sample to enable, for instance, study of particle density in the fluid sample in conjunction with a chemical content. More particularly, in this aspect the optical analysis system can be configured to operate in the transmission mode in which the light is shone through the sample to a similar detection system. Additionally, or alternatively, a mirrored surface can be placed within the transmissive sample to reflect the light back into the detection system as described above.

In another aspect of the disclosure, a method of determining information carried by light can include the steps of determining a plurality of orthogonal components of a first portion of a light signal, wherein each of the components has a predetermined shape with respect to a property of the first portion of the light signal that varies over a predetermined wavelength range; determining respective weightings for the orthogonal components so that the magnitude of the orthogonal components in the first portion of the light signal, weighted by the weightings, is proportional to the information present in the first portion in a predetermined relationship; providing an optical filter mechanism configured to optically filter the orthogonal components; disposing the optical filter mechanism to receive the first portion of the light signal; disposing a detector to receive a second portion of the light signal; detecting the property of the first portion of the light signal filtered by the optical filter mechanism; and analyzing the sample in real time by comparing the property of the first portion of the light signal to information in the second portion of the light signal.

In a further aspect of the disclosure, an optical analysis system includes a light source being configured to radiate a first light along a first ray path; a modulator disposed in the first ray path, the modulator being configured to modulate the first light to a desired frequency; a spectral element disposed proximate the modulator, the spectral element being configured to filter the first light for a spectral range of interest of a sample; a cavity in communication with the spectral element, the cavity being configured to direct the first light in a direction of the sample, the sample reflecting the first light as a second light, the cavity being further configured to direct the second light; a beamsplitter being configured to split the second light into a first beam and a second beam; an optical filter mechanism disposed to receive the first beam, the optical filter mechanism being configured to optically filter data carried by the first beam into at least one orthogonal component of the first beam; a first detector mechanism in communication with the optical filter mechanism to measure a property of the orthogonal component to measure the data; and a second detector mechanism being configured to receive the second beam for comparison of the property of the orthogonal component to the second beam.

In this aspect, the cavity includes a first region and a second region, the first region being configured to direct the second light in a direction of the beamsplitter, the second region being configured to direct the first light in a direction of the sample. Also in this aspect, the optical filter mechanism is a multivariate optical element.

Further in this aspect of the disclosure, the optical analysis system can include a gain mechanism in communication with at least one of the optical filter mechanism, the first detector mechanism and the second detector mechanism, the gain mechanism being configured to weight a magnitude of the property of the light orthogonal component. The optical analysis system can also include a mirror disposed proximate the cavity, the mirror being to direct the first light in the cavity in the direction of the sample. Furthermore, the optical analysis system can include a tube disposed about the mirror, the tube being configured to separate the first light from the second light.

In yet another aspect of the disclosure, an optical analysis system includes a light source being configured to radiate a first light along a first ray path; a modulator disposed in the first ray path, the modulator being configured to modulate the first light to a desired frequency; a spectral element disposed proximate the modulator, the spectral element being configured to filter the first light for a spectral range of interest of a liquid sample; a cavity in communication with the spectral element, the cavity being configured to direct the first light in a direction of the liquid sample; a conical mirror being configure to convert the first light reflecting from the liquid sample into a second light, the cavity being further configured to direct the second light; a beamsplitter being configured to split the second light into a first beam and a second beam; an optical filter mechanism disposed to receive the first beam, the optical filter mechanism being configured to optically filter data carried by the first beam into at least one orthogonal component of the first beam; a first detector mechanism in communication with the optical filter mechanism to measure a property of the orthogonal component to measure the data; and a second detector mechanism being configured to receive the second beam for comparison of the property of the orthogonal component to the second beam.

In this aspect of the disclosure, the conical mirror includes a coating of one of gold, aluminum or other element or material selected based on desired spectral region.

In an additional aspect of the disclosure, an optical analysis system includes a light source being configured to radiate a first light along a first ray path; a modulator disposed in the first ray path, the modulator being configured to modulate the first light to a desired frequency; a spectral element disposed proximate the modulator, the spectral element being configured to filter the first light for a spectral range of interest of a sample; a cavity in communication with the spectral element, the cavity being configured to direct the first light in a direction of the sample; a conical mirror being configured to convert the first light reflecting from the sample into a second light, the cavity being further configured to direct the second light; a beamsplitter being configured to split the second light into a first beam and a second beam; an optical filter mechanism disposed to receive the first beam, the optical filter mechanism being configured to optically filter data carried by the first beam into at least one orthogonal component of the first beam; a first detector mechanism in communication with the optical filter mechanism to measure a property of the orthogonal component to measure the data; a second detector mechanism being configured to receive the second beam for comparison of the property of the orthogonal component to the second beam; an accelerometer being configured to control the data acquisition such that only detector signals during the period of time when the system is in the proper orientation such that the material sample (e.g., aspirin) is in proximity to the interrogation window are used for calculation; a computer having a data acquisition and conversion card, the computer disposed in the system in communication with the first and second detector mechanisms for signal processing; and a battery and charging system disposed in the system in electrical communication with the system to provide stand-alone operation capability.

Other features and aspects of the disclosure are discussed in greater detail below.

BRIEF DESCRIPTION OF THE DRAWINGS

A full and enabling disclosure of the present disclosure, including the best mode thereof to one skilled in the art, is set forth more particularly in the remainder of the specification, including reference to the accompanying figures, in which.

DETAILED DESCRIPTION OF THE DISCLOSURE

Figure 1:
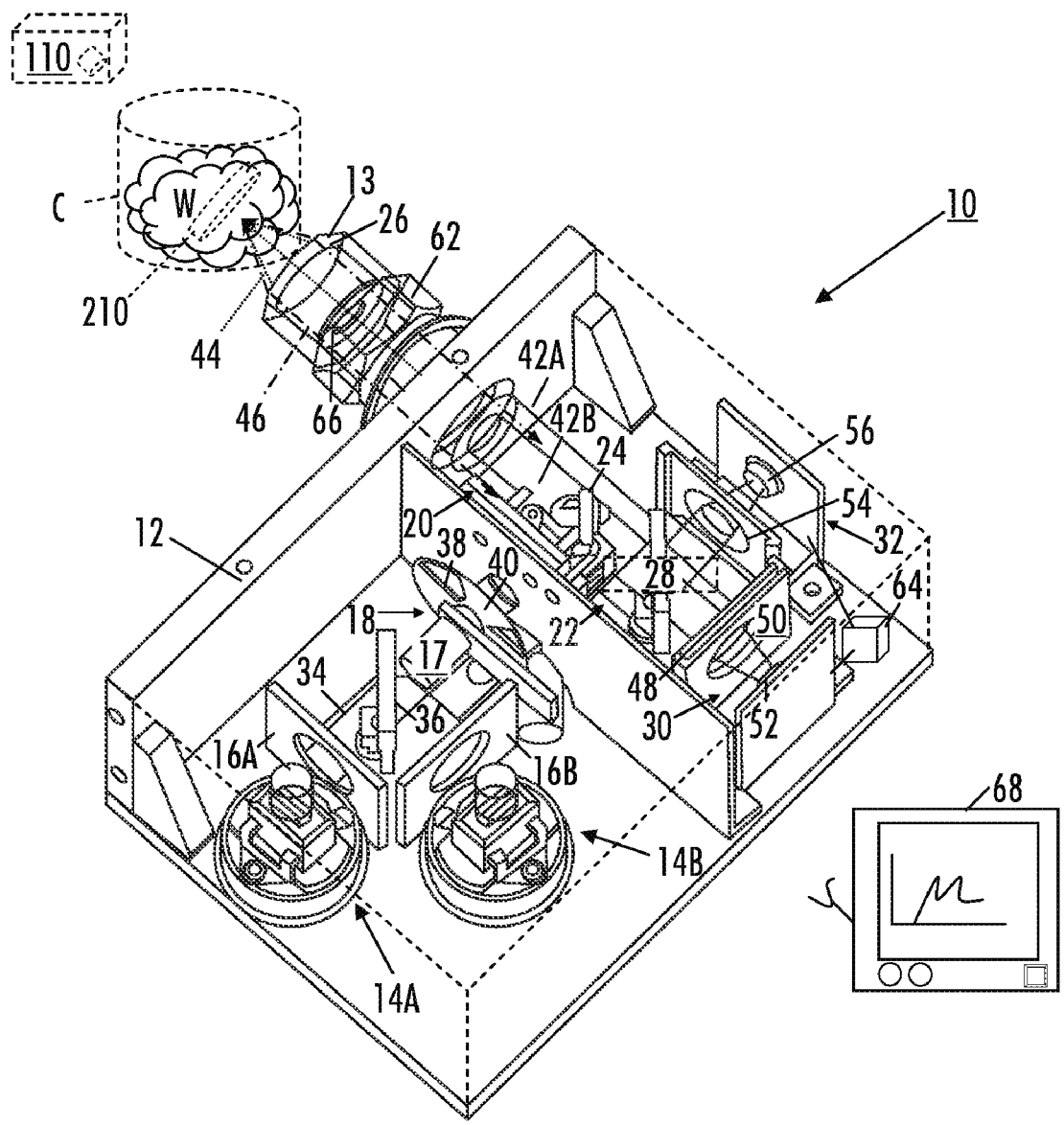
FIG. 1 is a top perspective view of one embodiment of a real time measurement system according to an aspect of the present disclosure.

Detailed reference will now be made to the drawings in which examples embodying the present inventions are shown. The detailed description uses numerical and letter designations to refer to features of the drawings. Like or similar designations of the drawings and description have been used to refer to like or similar parts of the disclosure.

The drawings and detailed description provide a full and written description of the examples in the disclosure, and of the manner and process of making and using those examples, so as to enable one skilled in the pertinent art to make and use them, as well as the best mode of carrying out the examples. However, the examples set forth in the drawings and detailed description are provided by way of explanation only and are not meant as limitations of the disclosure. The present disclosure thus includes any modifications and variations of the following examples as come within the scope of the appended claims and their equivalents.

Figure 2:
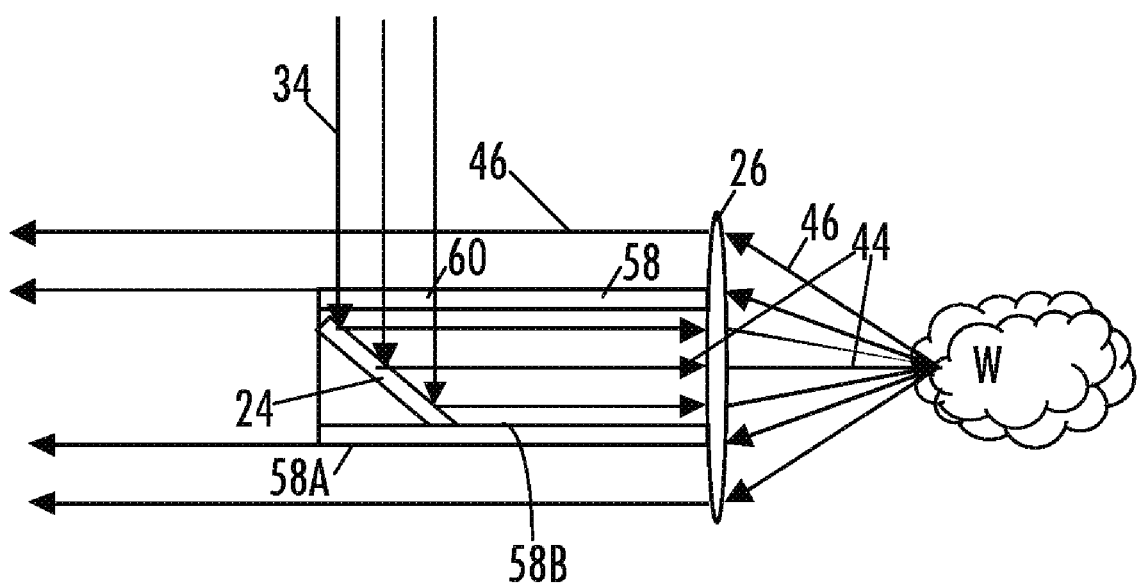
FIG. 2 is a schematic view of a concentric cavity as in FIG. 1 in accordance with a further aspect of the present disclosure.

As generally shown in FIGS. 1 and 2, an optical analysis system according to an aspect of the disclosure is designated by the element number 10. The system 10 is designed around at least one application specific multivariate optical element (MOE) based on spectra typically provided by an end-user. System design takes into account representative spectra of compounds of interest, basic and expected concentrations of interest across a range of expected interferents. Also, the system 10 incorporates the desired spectral regions (UV, VIS, NIR, MIR, IR) of interest.

In the embodiment shown in FIG. 1, the optical analysis system 10 broadly includes a housing 12, a plurality of illumination or light sources 14A, 14B, a concentric light tube or cavity 22, a focusing lens 26, at least one beam splitter 28, a first detector 30 including a multivariate optical element 48 and a second detector 32. Although FIG. 1 shows a generally square- or rectangle-shaped, metallic housing 12 and two detectors 30, 32 arranged therein, the skilled artisan will instantly appreciate that a variety of shapes, dimensions, component placements and material makeup of the components can be substituted for the examples shown according to various requirements such as government regulations, customer specifications and the like.

As used herein, the term "light" is broadly used to mean any form of radiation or radiative energy including, for instance, visible light or light in the infrared region. "Light" is also referred to herein as a light signal, a light beam, a light ray and the like to mean any form of radiative energy in the electromagnetic spectrum. Similarly, the term "transmission" can mean transmission of radiative energy onto a surface of a sample; penetration, however slight, into a sample such as a particulate sample or opaque fluid sample; or passage through a sample such as a fluid sample.

Moreover, as discussed below with respect to another embodiment of the disclosure, a workpiece or sample W can be analyzed using a PCR-type model without the beamsplitter 28 in an off-line approach. As used herein, the workpiece or sample W can mean an analyte undergoing analysis over a range of conditions. The sample can be a solid or a fluid including but not limited to a powder, a pharmaceutical powder mixed with lactose and other excipient materials, a chemical, a polymer, a petroleum product, a solution, a dispersion, an emulsion and combinations of these solids and fluids.

The skilled artisan will also understand that although the system can be a measurement system operating in reflectance mode, the system can also be configured to operate in a transmission mode in which light is shone through the sample W from an incident side of the sample W to a similar detection system 110 on another side of the sample W. Alternatively, or additionally, a mirrored surface 210 can be placed within the transmissive sample to reflect the light back into the detection system 10. Therefore, the disclosure is not limited only to the examples shown in the figures.

With more particular reference to FIG. 1, the housing 12 (shown partially in phantom for clarity) can be metal such as stainless steel, a plastic material such as high-density polyethylene (HDPE) or any durable material for protecting the components of the optical analysis system 10. As shown, sampling of the sample W is accomplished through a window 13 in the enclosed optical analysis system 10. Accordingly, the enclosed optical analysis system 10 can be used in a dangerous (e.g., explosive) environment. As will be described in detail below, the window 13 is transmissive in a known manner in a spectral region of interest.

As briefly introduced above, the illumination sources 14A, 14B are chosen to provide a source light 34, which has a spectral range determined by a spectral range of interest for the intended sample measurement. The illumination sources 14A, 14B are also chosen based on reliability, intensity, temperature generation, and other factors. The illumination sources 14A, 14B are also redundant to further enhance reliability. As shown in FIG. 1, the redundant illumination sources 14A, 14B can be oriented at 90 degrees from each other with a "50-50" beam splitter 36 located near their center point to provide a constant source of illumination.

FIG. 1 further shows a plurality of lenses 16A, 16B, respectively associated with each of the illumination sources 14A, 14B. The lenses 16A, 16B are used to collect the light signal 34 from the illumination sources 14A, 14B and to focus the light signal 34 on a modulator or chopper wheel 18, described below. As shown, the lenses 16A, 16B are positioned to capture as much of the light signal 34 as possible from the illumination sources 14A, 14B. Additionally, a chopper-focusing lens 17 is used to focus as much of the light signal 34 as possible through the chopper wheel 18. The skilled artisan will instantly recognize the lenses 16A, 16B, 17 are selected for focal length, position, material of construction and the like to enhance transmission (reduce loss) of the light signal 34. For example, in the design of the optical path, if the illumination sources 14A, 14B is a lamp, slight magnification or demagnification of the source is generally obtained at the sample W, depending on the ratios of the focal length, e.g., of the lens 16A to that placed after the illumination source 14A to collimate it. Ultimately, the image of the illumination source 14A on the sample W is directed toward the detectors 30, 32 as described below and again with some slight magnification or demagnification, depending on the ratios of the focal length, e.g., of the lenses 16A, 16B to that of, e.g., a lens 50 placed before the detector 30 to focus a reflected light 46 onto the detector 30. Thus, it should be understood that there is a relationship between the focal lengths of the lenses 16A, 16B that must be maintained in order to make sure the ultimate image of the source-excited region of the sample W that is formed on the detectors 30, 32 is suited to the physical dimensions of the detectors 30, 32.

The skilled artisan will further appreciate that the lenses 16A, 16B shown for example in FIG. 1 are plastic, Fresnel lenses well suited for use in an infrared (IR) region of about 1000 nanometers (nm) to about 3000 nm. However, the skilled artisan will understand that the lenses 16A, 16B are not limited to only plastic, Fresnel lenses and that other types of lenses and materials such as glass can be used for these lenses.

As further shown in FIG. 1, the chopper wheel 18 includes a plurality of alternating windows 38 and a plurality of alternating spokes 40. The alternating windows 38 and spokes 40 modulate the light signal 34 from about 50 Hertz (Hz) to about 5000 Hz to enable a plurality of photodetectors 52, 56 in the optical system 10 to perform properly, as will be further described below. As shown in this example, the chopper wheel 18 is a 10-window chopper wheel rotating at 40 Hz, which provides a chopped signal of 400 Hz. The number and arrangement of the windows 38 and spokes 40 and thus, the chopper frequency, are chosen based on several variables, including a rate of motion of the sample material W moving past the sampling window 13; a performance characteristic of the photodetectors 52,56 and amplification system; a predetermined sampling rate of the data collection and analysis system 10; physical properties of a chopper motor (not shown), control system (not shown), and the chopper wheel 18 (including material(s) of the windows 38).

More particularly, the number of windows 38 in the chopper wheel 18 can be adjusted to provide a suitable degree of signal modulation. In one aspect of the disclosure, the chopper wheel 18 has open windows 38 and black spokes 40, which block the light signal 34. In another aspect, different materials can be placed in the windows 38 to provide different spectral characteristics for the various windows 38. Moreover, the transmission characteristic of these windows 38 could be used as further spectral elements. The windows 38 can also contain multivariate optical elements (MOE) such as those described below with respect to a MOE 48 of the MOE detector 30.

FIG. 1 also shows a plurality of bandpass filters or spectral elements 20 located in a path of the light signal 34 after the light signal 34 has passed through the chopper wheel 18. As briefly discussed above, the spectral elements 20 are selected based on a desired application; i.e., to analyze a particular sample W. The spectral elements 20 are chosen so that the spectral region of illumination covers the desired range; i.e., related to a particular chemical material of interest. For example, if 1500-2000 nanometers (nm) of light wavelengths is the desired spectral region, the spectral elements 20 are selected to filter out wavelengths are not in that region. An example of these spectral elements is a SCHOTT brand filter, which can be a long pass, short pass, or band pass filter. By way of further example but not of limitation, some suitable materials for use as the spectral elements 20 are listed in the following table.

TABLE 1

Properties of Select Transmitting Materials

| Material | Comments | SWL cm-1 | LWL cm-1 | RI | Solubility g/100 g | Hardness Kg/mm 2 | MP °C. | pH Range |
|---|---|---|---|---|---|---|---|---|
| AMTIR | SeAsGe glass | 11000 | 593 | 2.5 | 0 | 170 | 370 | 1-9 |
| BaF 2 | Barium Fluoride | 66600 | 691 | 1.45 | 0.17 | 82 | 1280 | 5-8 |
| Ca F 2 | Calcium Fluoride | 79500 | 896 | 1.4 | 0.0017 | 158 | 1360 | 5-8 |
| CsI | Cesium Iodide, very hygroscopic | 42000 | 172 | 1.73 | 44 | 20 | 621 | NA |
| Diamond | Type IIa, strong IR absorbance between 2700-1800 cm−1 | 30000 | <2 | 2.4 | 0 | 5700 | 550fp | 1-14 |
| Ge | Germanium, becomes opaque at elevated temperatures | 5500 | 432 | 4 | 0 | 780 | 936 | 1-14 |
| KBr | Potassium Bromide | 48800 | 345 | 1.52 | 53 | 6 | 730 | NA |
| KCl | Potassium Chloride | 55600 | 385 | 1.45 | 35 | 7 | 776 | NA |
| KRS-5 | Thallium Bromide/ Thallium Iodide | 17900 | 204 | 2.37 | 0.05 | 40 | 414 | 5-8 |
| NaCl | Sodium Chloride | 52600 | 457 | 1.49 | 36 | 18 | 801 | NA |
| Polyethylene | For Far-IR, swells with some organic solvents | 625 | <4 | 1.52 | 0 | | 110 | 1.5-14 |
| SiO2 | Silicon Dioxide | 50000 | 2315 | 1.53 | 0 | 460 | 1713 | 1-14 |
| Si | Silicon, strong IR absorbance between 624-590 cm−1 | 8900 | 624,30 | 3.41 | 0 | 1150 | 1420 | 1-12 |
| ZnS | Zinc Sulfide | 17000 | 690 | 2.2 | 0 | 240 | 1830 | 5-9 |
| ZnSe | Zinc Selenide | 15000 | 461 | 2.4 | 0 | 120 | 1526 | 5-9 |

Note:
To convert from wavenumber (cm-1) to wavelength (μm), divide 10,000 by the wavenumber; e.g., 5500 cm-1 is equivalent to 1.8 μm or 1800 nm.
SWL—Shortest wavelength for transmission, 1 mm, 50% transmission
LWL—Longest wavelength for transmission, 1 mm, 50% transmission
RI—Refractive Index, at relevant wavelength
MP—Melting point With reference now to FIGS. 1 and 2, the light signal 34 exits the spectral elements 20 and reflects off a first mirror or turning mirror 24. It will be appreciated that although the turning mirror 24 is shown at an angle of about 45 degrees with the light signal 34 reflecting at this angle, the turning mirror 24 can be turned to any desired angle. As known to those skilled in the art, the turning mirror 24 can be a powered turning mirror powered by a battery, by electricity or the like. Further description of power sources and implementation with the turning mirror 24 is not necessary for one skilled in the art to understand this aspect of the disclosure. The skilled artisan will further appreciate that although the turning mirror 24 is shown as a unitary mirror, multiple mirrors can be utilized and arranged in, or adjustable to, a variety of positions.

As further shown in FIGS. 1 and 2, the filtered and reflected light signal 34 becomes a reflected light 44 after being reflected by the turning mirror 24. The reflected light 44 thus continues down the concentric sampling tube 22, briefly introduced above, in a direction of the sample W. As shown and further described below, the concentric tube 22 includes an inner annular region (also referred to as tube or chamber) 42A and an outer annular region 42B (also, tube or chamber). In this example, the reflected light 44 is reflected along the inner annular region 42A. It will be understood that the illumination sources 14A, 14B and the detectors 30, 32 are shown in an exemplary orientation and can be reversed. It will be further appreciated that the light signal 34 and the reflected light 44 are shown collimated for simplicity. However, the light signal 34 and the reflected light 44 may not be completely collimated because the illumination sources 14A, 14B can be extended rather than point sources.

The focusing lens 26 in FIGS. 1 and 2 is located near an end of the tube 22 proximate the sample W. As shown in this example, the end of the tube 22 is sealed with the transmissive window 13. The transmissive window 13 should be uniformly transmissive across wavelengths, but if it is not, the transmission characteristics of the transmissive window 13 are taken into account for the design of the system 10 and in particular the MOE 48. This embodiment may include an additional focusing lens 66, which can be solid or have one or more apertures as shown in FIG. 1. The additional focusing lens 66 is used to focus or collimate a carrier light 46, described below, in a direction of the tube 22.

As further shown in FIGS. 1 and 2, the focusing lens 26 focuses the reflected light 44 onto, into or near the sample W via the transmissive window 13. In this example, the reflected light 44 is focused with a focal point 0-5 mm into the sample W. In addition to isolating components of the optical analysis system 10 from an external environment, the transmissive window 13 further enables a mixing vessel or container C, which is being tested/sampled into, to remain intact. As shown in this example, a one-inch (inner diameter) Swagelok® brand connector 62, available from Swagelok Corporation, Solon, Ohio, is used to connect the optical analysis system 10 to the mixing vessel C. This arrangement permits the reflected light 44 to be sent down the tube 22 (inner region 42A), interact with the material of interest W, reflect back up the tube 22 (outer region 42B), and be directed to the detectors 30, 32 as further described below.

As most clearly shown in FIG. 2, a tube 58 defines an aperture 60 for passage of the light signal 34 in a direction of the turning mirror 24. Separation of the illumination and reflection light paths or signals 44, 46 can be further defined or separated by physically separating the inner and outer regions 42A, 42B employing the tube 58. Any minimal reduction in light return of the carrier light 46 described below (caused by physical occupation of a portion of the outer region 42B by the tube 58) is offset by improvement in the amount of backscattered radiation returned to the detectors 30, 32 without encountering the sample W.

More specifically, the tube 58 is used to reduce a non-zero background measurement. The non-zero background measurement can occur in an optical system when a small amount of scattered light is returned to a detector even when no sample is present. Some of the scattered light can be reflected from a window, and some can come from the lenses themselves.

FIG. 2 shows that the tube 58 placed around the mirror 24 before the lens 26. The tube 58 reduces background signals by separating the excitation and collection light paths 34, 46 to minimize "cross-talk". As shown, the tube 58 defines an aperture 60 for passage of the light signal 34 in a direction of the turning mirror 24. As further shown, a conical extension 58A of the tube 58 can be placed after the mirror 24 in a direction of the detector 30. A thickness of the tube 58 should be minimized.

Also shown in FIG. 2, the tube 58 can have specular interior and exterior surfaces as well as a highly reflective coating 58B, such as gold, applied by electrolysis deposition, evaporation or other thin film coating method. The coating 58B reflects rays 34, 46 that would ordinarily terminate at a surface of the tube 58 back into respective optical paths from which they came. An image of the illumination source 14A, 14B may be vignetted, but the "lost" light in the image is still focused to a spot within the zone illuminated by the illumination source 14A, 14B. Likewise, the returning light outside the tube 58 can be kept from being lost by traveling inside an outer tube with a specular reflecting surface (not shown, but surrounding the outer light path). This will keep light loss to a minimum while keeping the input and output paths relatively isolated from one another.

As introduced above, the reflected light 46 shown in FIGS. 1 and 2 travels back down the outer annular region 42A of the sampling tube 22, past the turning mirror 24. The light 46 reaches the beam splitter 28 (one of its operating positions shown in phantom). The beam splitter 28 divides the light 46 with a neutral or gray spectrum, sending some of the light 46 in a direction of the first or Multivariate Optical Element (MOE) detector 30 through the MOE 48, briefly introduced above, and through a first lens 50 onto the photo detector 52, also briefly introduced above. The beam splitter 28 sends some other portion of the light 46 through a second lens 54 onto the other detector 56, also briefly introduced above.

As shown in the following table by example but not of limitation, some detectors suitable for use as the detectors 52, 56 include:

TABLE 2

| Detector | Types[1] | Wave Range ($\lambda\mu$) | Detectivity $D^2$ | Cut Off Frequency ($H_z$) | Operating Temperature (K) |
|---|---|---|---|---|---|
| Pt-S | PV | 0.35-0.6 | 30 | $10^8$ | 295.0 |
| Si p-n PD | PV | 0.4-1.0 | 50 | $10^7$ | 295.0 |
| Si p-i-n PD | PV | 0.4-1.1 | 80 | $10^8$ | 295.0 |
| Si APD | PV | 0.4-0.8 | 80 | $10^{10}$ | 295.0 |
| Ge p-n PD | PV | 0.6-1.8 | 50 | $10^7$ | 295.0 |
| InSb p-n PD | PV | 3.0-6.2 | 8 | $5 \times 10^2$ | 77.0 |
| PbSnTe p-n PD | PV | 5.0-11.4 | >15-60 V/W | 10 | 77.0 |
| PbS | PC | 0.5-3.8 | 15.00 | 300 | 196.0 |
| PbSe | PC | 0.8-4.6 | 3.00 | $3 \times 10^3$ | 196.0 |
| PbTe | PC | 0.8-5.5 | 0.16 | $3 \times 10^3$ | 196.0 |
| p-InSb | PC | 2.0-6.7 | 2.00 | $2 \times 10^5$ | 77.0 |
| n-InSb | PC | 1.0-3.6 | 30.00 | $2 \times 10^6$ | 195.0 |
| PbSnTe | PC | 5.0-11.0 | 1.7 | $8 \times 10^5$ | 4.2 |
| CdHgTe | PC | 5.0-16.0 | 3.00 | $10^4$ | 4.2 |
| Ge:Au | PC | 2.0-9.5 | 0.02 | $10^4$ | 77.0 |
| Ge:Zn,Au | PC | 5.0-40.0 | 1.00 | $10^3$ | 4.2 |
| Ge:Cu | PC | 5.0-30.0 | 3.00 | $10^3$ | 4.2 |
| Si:Al | PC | 2.0-16.0 | 1.00 | $10^4$ | 27.0 |
| Si:Sb | PC | 2.0-31.5 | 1.80 | $10^4$ | 4.0 |
| ATGS | TC | 1-1000 | 0.030 | 10 | 295.0 |
| (Ba,Sr)TiO$_3$ | TC | 1-1000 | 0.011 | 400 | 295.0 |
| Si | — | 0.2-1.1 | — | — | — |

TABLE 2-continued

| Detector | Types[1] | Wave Range (λμ) | Detectivity D[2] | Cut Off Frequency (H_z) | Operating Temperature (K) |
|---|---|---|---|---|---|
| Ge | — | 0.4-1.8 | — | — | — |
| InAs | — | 1.0-3.8 | — | — | — |
| InGaAs | — | 0.8-3.0 | — | — | — |
| InSb | — | 1.0-7.0 | — | — | — |
| InSb (77K) | — | 1.0-5.6 | — | — | — |
| HgCdTe (77K) | — | 1.0-25.0 | — | — | — |

Note
[1] PV - photo transistor type; PC: photo conductive detector type; TC: pyroelectric detector type Note
[2] ($10^{10}$ cmHz$^{1/2}$ W$^1$)

As further shown in FIG. 1, a gain mechanism 64 is in communication with the detectors 30, 32 and the MOE 48. The gain mechanism 64 weights a magnitude of the property of an orthogonal component of a portion of the carrier light 48 as described, for instance, by Myrick et al. in U.S. Pat. No. 6,198,531 B1 and in U.S. Pat. No. 6,529,276 B1 to Myrick.

As briefly introduced above, the beam splitter 28 is not required in an alternative embodiment of the disclosure in which a signal from the sample W is analyzed using a PCR-type model in an off-line approach. This alternative embodiment and approach is useful, for instance, for studying signals independently. More particularly, a system substantially as described above but without the beam splitter 28 is used to take an integral of the light on a detector similar to the detector 30 described above. By analyzing frequency-dependent intensities, results similar to those of the foregoing embodiment are produced, although possibly with a relatively slower response time in the present embodiment.

Also, in an additional aspect of the disclosure as shown in FIG. 1, a system 68 using an electrochemical or chemometric model can be employed in conjunction with any of the foregoing embodiments to make similar or same measurements of the light 46 reflected from the sample W as the measurements described in the foregoing embodiments. By way of example but not of limitation, the system 68 may be one as described by Myrick et al. in PCT Application Number PCT/US2004/043742, based on U.S. Provisional Application No. 60/533,570, filed Dec. 31, 2003, which are incorporated herein by reference to these applications.

In addition to the reflectance mode described above, one or more optical analysis systems can operate in a transmission mode in conjunction with the foregoing embodiments. In such a case, light is directed (passes) through the sample W, e.g., a fluid sample, and collected on another side of the sample W to enable study of particle density in the fluid in conjunction with the chemical content described above. For instance, the system 10 can be configured to operate in transmission mode where the light is shone through the sample W to a similar detection system 110 as shown in FIG. 1 in phantom for clarity). Additionally, or alternatively, a mirrored surface 210 can be placed within the transmissive sample W to reflect the light back into the system 10.

Figure 3:
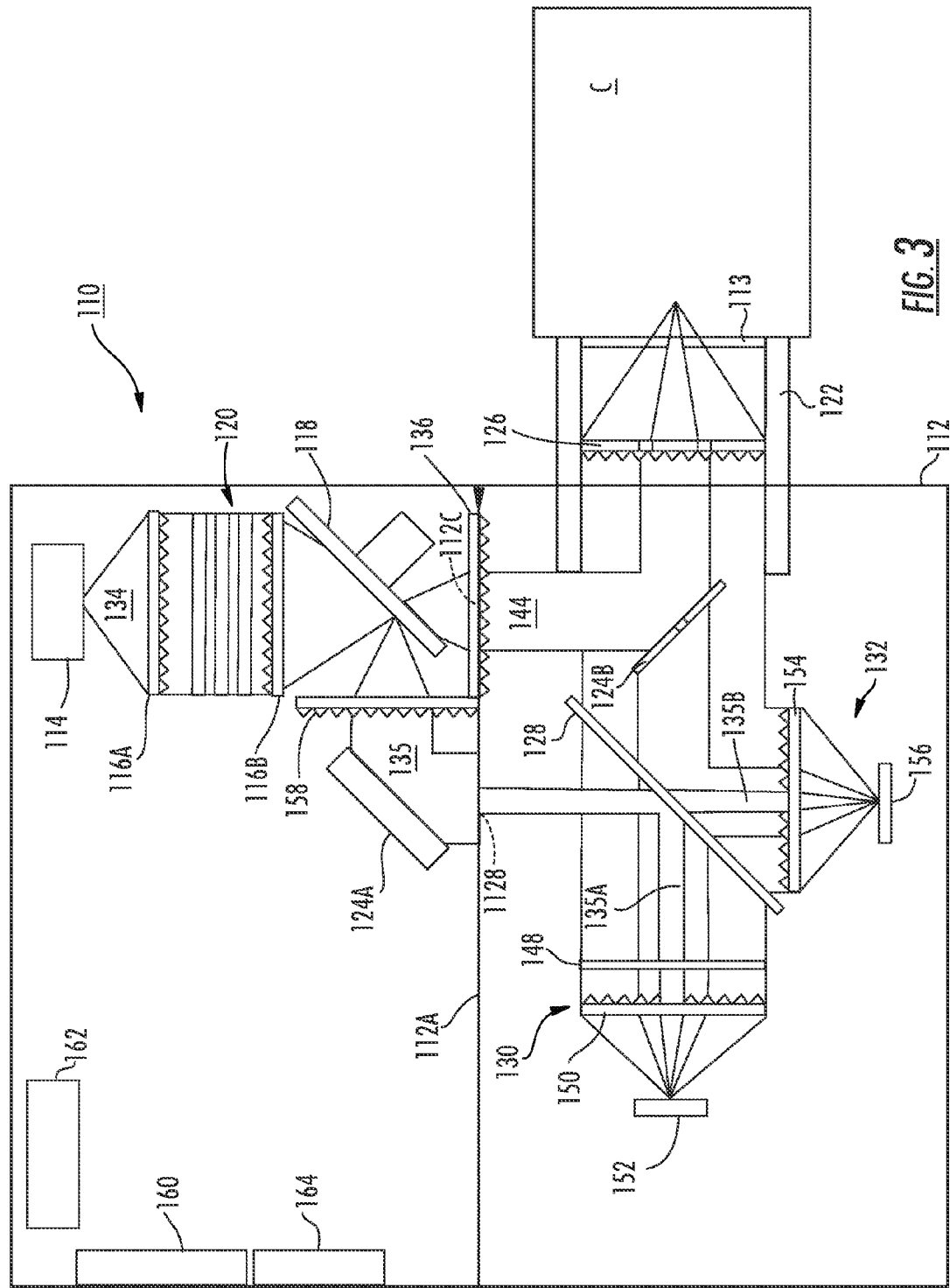
FIG. 3 is schematic plan view of another embodiment of a real time measurement system according to another aspect of the present disclosure.

With reference now to FIG. 3, a second exemplary embodiment of the present subject matter is designated generally by reference number 110. Many aspects of the optical analysis system 110 and related components are similar to the foregoing embodiment; thus, for the sake of brevity, only certain differences are described below. However, to provide a full and enabling disclosure of the optical analysis system 110, when like or similar elements and components are not specifically described below; implicit reference is made to the foregoing descriptions.

As shown in FIG. 3, the optical analysis system 110 broadly includes a housing 112, an illumination or light source 114, a chopper wheel 118, one or more spectral elements 120, a focusing lens 126, a beam splitter 128, a first detector 130 including a multivariate optical element 148, and a second detector 132. The optical analysis system 110 further includes an electrical connection 160, a pressurization sensor 162 and a purge gas assembly 164, which those skilled in the art will readily understand; therefore, further description is not necessary to understand and practice these aspects of the disclosure.

With more particular reference to FIG. 3, the illumination source 114 provides a light 134, which passes through a collecting Fresnel lens 116A and into and through the spectral element(s) 120. In this example, the illumination source 114 is rated for at least about 10,000 hours of operation, which alleviates a need for redundant illumination sources though they may be provided if desired. Also in this example, the collecting Fresnel lens 116A is sized to be about 1.5 square inches and is spaced about 0.6 inches from the illumination source 114. The skilled artisan will instantly recognize that these dimensions can be adjusted according to particular system requirements and are not meant as limitations of the disclosure.

As further shown in FIG. 3, the light 134 passes through the spectral elements 120, which filter out undesired wavelengths to define a desired spectral region, e.g., 1500-2000 nm, in order to target a particular chemical material of interest. The light 134 is focused by focusing Fresnel lens 116B, which is also sized to be about 1.5 square inches and spaced about 1 inch from the chopper wheel 118. As shown, the chopper wheel 118 reflects a portion of light 134 as a calibration or reference light 135 and a transmitted light 144. Calibration light 135 is collimated by lens 158 before reflecting from a first mirror 124A through an adjustable aperture 112B in a bulkhead 112A of the housing 112. The aperture 112B is adjustable to dictate a desired amount of the calibration light 135. Finally, calibration light 135 impinges on beam splitter 128 thereby sending a portion 135A of calibration light 135 to the first MOE detector 130 and a portion 135B of calibration light 135 to the second or baseline detector 132.

FIG. 3 further illustrates that transmitted light 144 passes from the chopper wheel 118 into a collimating Fresnel lens 136, which in this example is sized to be about 1.5 square inches and is spaced about 0.6 inches from the chopper wheel 118. The transmitted light 144 passes through another adjustable aperture 112C in the bulkhead 112A and impinges upon a second mirror 124B, which directs the transmitted light 144 toward a sample in a container C, such as mixing vat or blender. The skilled artisan will recognize that the container could be a conveyor belt or other device for holding or transporting the sample and is not limited to an enclosed container.

As shown in FIG. 3, the transmitted light 144 is focused by the focusing Fresnel lens 126, which in this example may be round and about 15/16 inches in diameter and is adjustable with an inner tube 122. Also in this example, lens 126 may be positioned about 0.6 inches from an outer surface of the container C. As shown, the transmitted light 144, now focused, passes through a transmissive window 113, which in this example is approximately 1 inch in diameter and with an anti-reflective (AR) coating disposed on one or both sides of the lens 126. The AR coating ensures that a chemical process in the container C does not interfere with the measuring process of the optical analysis system 110. Thus, the transmitted light 144 enters the container C and reflects from the sample as a carrier light 146. The sample can be a moving mixture such as aspirin and an excipient being blended in real time, or a plurality of tablets passing by on a conveyor belt at high speed.

FIG. 3 further illustrates that the carrier light 146 is directed by the tube 122 in a direction of the first detector 130. Eventually, the carrier light 146 impinges on the beam splitter 128 and a portion passes in a direction of the detector 132 for baselining with the portion 135B of the calibration light 135. Another portion of the carrier light 146 passes through MOE 148, which as noted above, has been selected for the chemical of interest based on the various components of the system 110. Finally, that portion of the carrier light 146, having passed through the MOE 148, is focused by lens 150 and received by the detector 152. As described above, the two signals collected by the detectors 132 and 152 can be manipulated, e.g., mathematically, to extract and ascertain information about the sample carried by the carrier light 146.

Figure 4A:
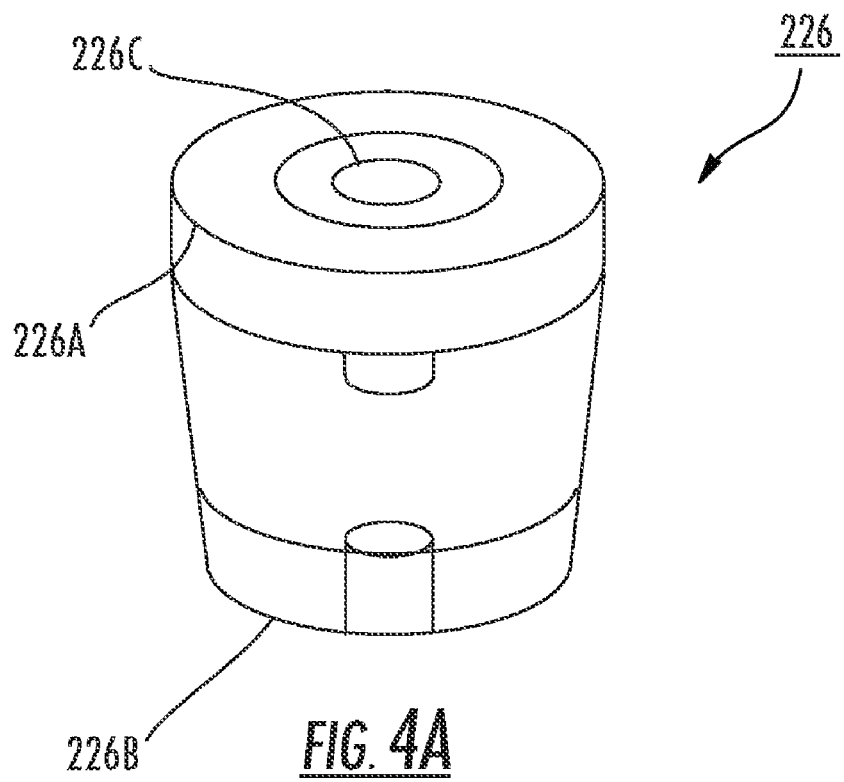
FIG. 4A is a perspective view of a retroreflecting mirror for use in the embodiments of FIGS. 1-3 according to a further aspect of the disclosure.
Figure 4B:
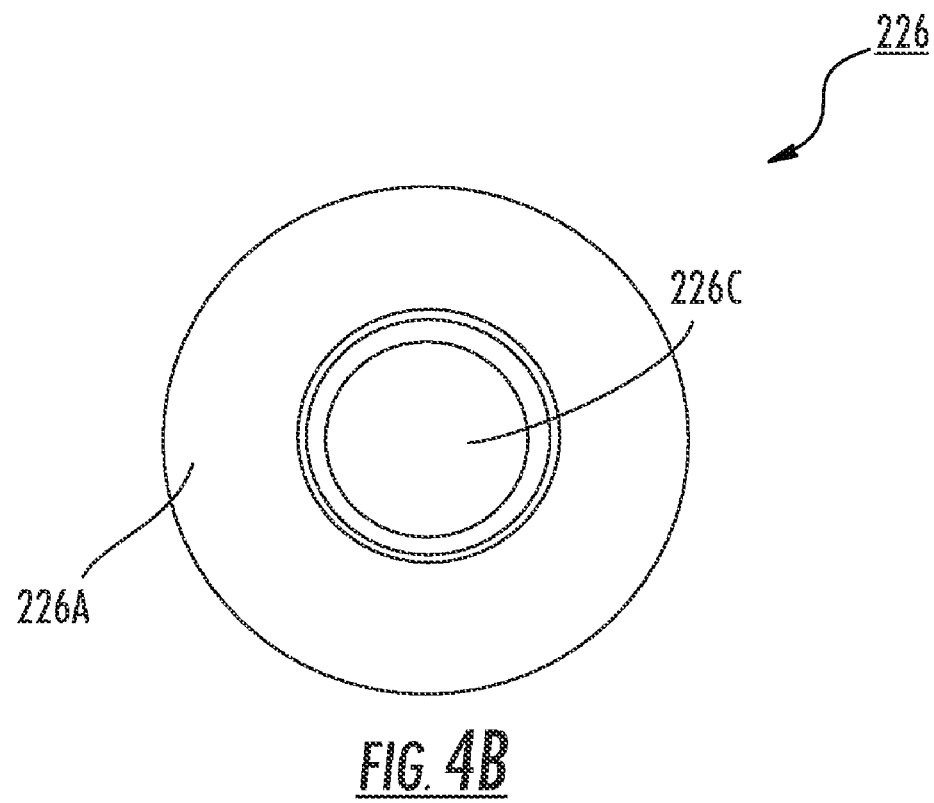
FIG. 4B is an end view of the retroreflecting mirror as in FIG. 4A.

Turning now to FIGS. 4A and 4B, detailed views of a retroreflector or collimating mirror 226 are shown. In this example, the mirror 226 has a first end 226A and a second end 226B and is generally cylindrically shaped. The mirror 226 is also coated with a reflective surface such as aluminum (Al), gold (Au) or other elements or materials dictated by the desired spectral region. The skilled artisan will appreciate that other shapes and reflective coatings can be provided to meet specific design requirements and characteristics of the target sample; thus, the mirror 226 is not limited to the exemplary embodiment shown in FIGS. 4A and 4B.

With reference to FIGS. 3, 4A and 4B, the mirror 226 is useful for analyzing translucent liquids, for example, since liquids, in contrast to powders, do not readily create a diffuse reflectance to produce the desired carrier light 146 as shown in FIG. 3. By way of example operation, the lens 126 in FIG. 3 may be removed and replaced with the mirror 226 for retroreflection of the light 144 for transreflection measurement of the carrier light 146 for liquid sample analysis.

Figure 5:
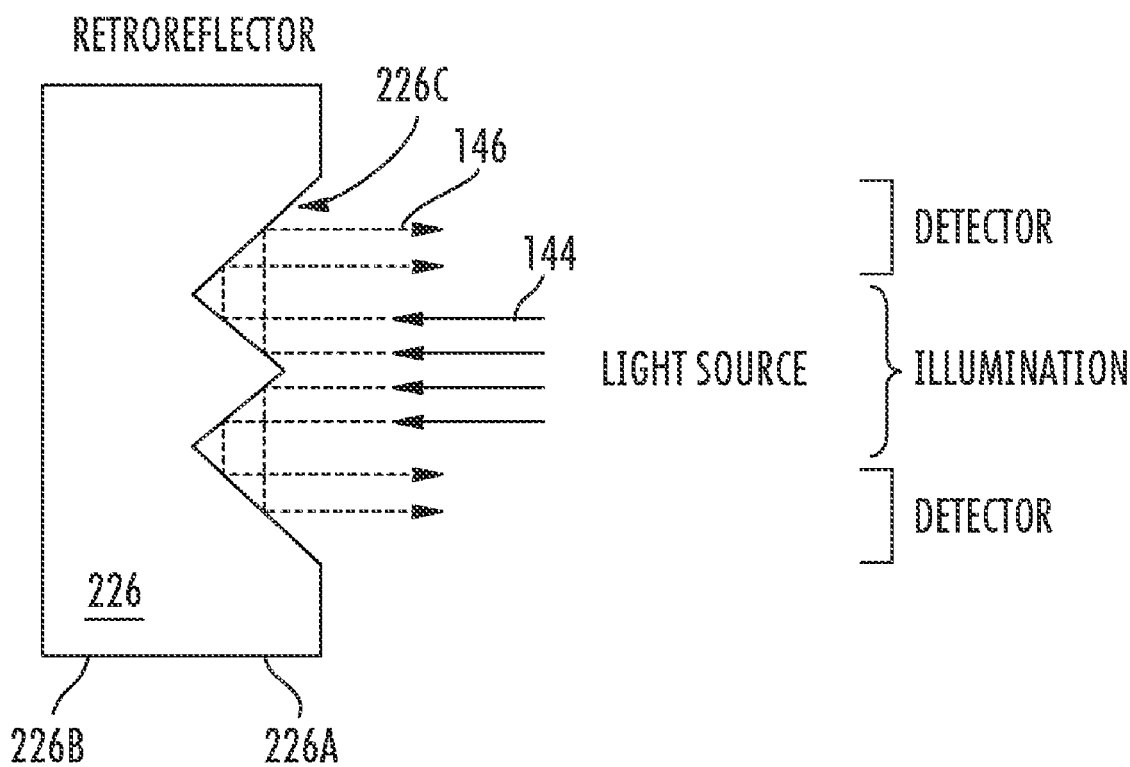
FIG. 5 is a cross section of the retroreflecting mirror taken along lines V-V in FIG. 4B.
Figure 9:
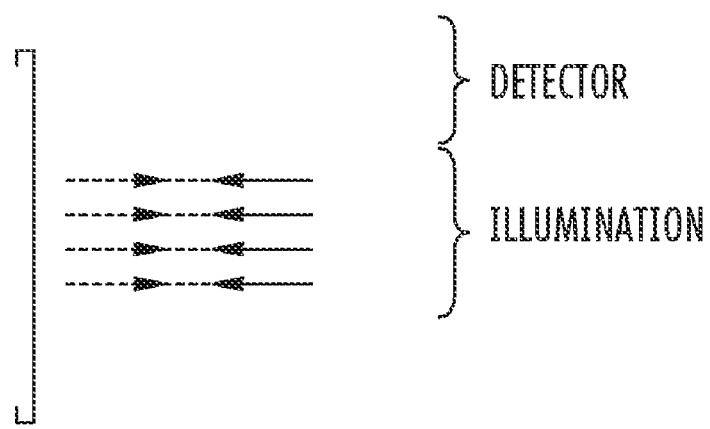
FIG. 9 is a partial, schematic view of a conventional mirror.

As shown in the cross section of FIG. 5, as the light 144 passes through the mirror 226, the light 144 is collimated into the liquid sample in the container C. The carrier light 146 reflects from the liquid sample and returns through the first end 226A, which defines one or more conical shaped depressions or indentations 226C. The conical shaped indentations 226C act to direct the carrier light 146 in a manner similar to the example shown in FIG. 3. Accordingly, a portion of the carrier light 146 is directed through the MOE 148 as described above. In contrast, a flat mirror as shown in FIG. 9 would reflect a light ray back along a same ray path as an illumination source such that any information carried by the reflected light ray would at least interfere with the illumination source but possibly be unreadable by a detector offset from illumination source.

Figure 6A:
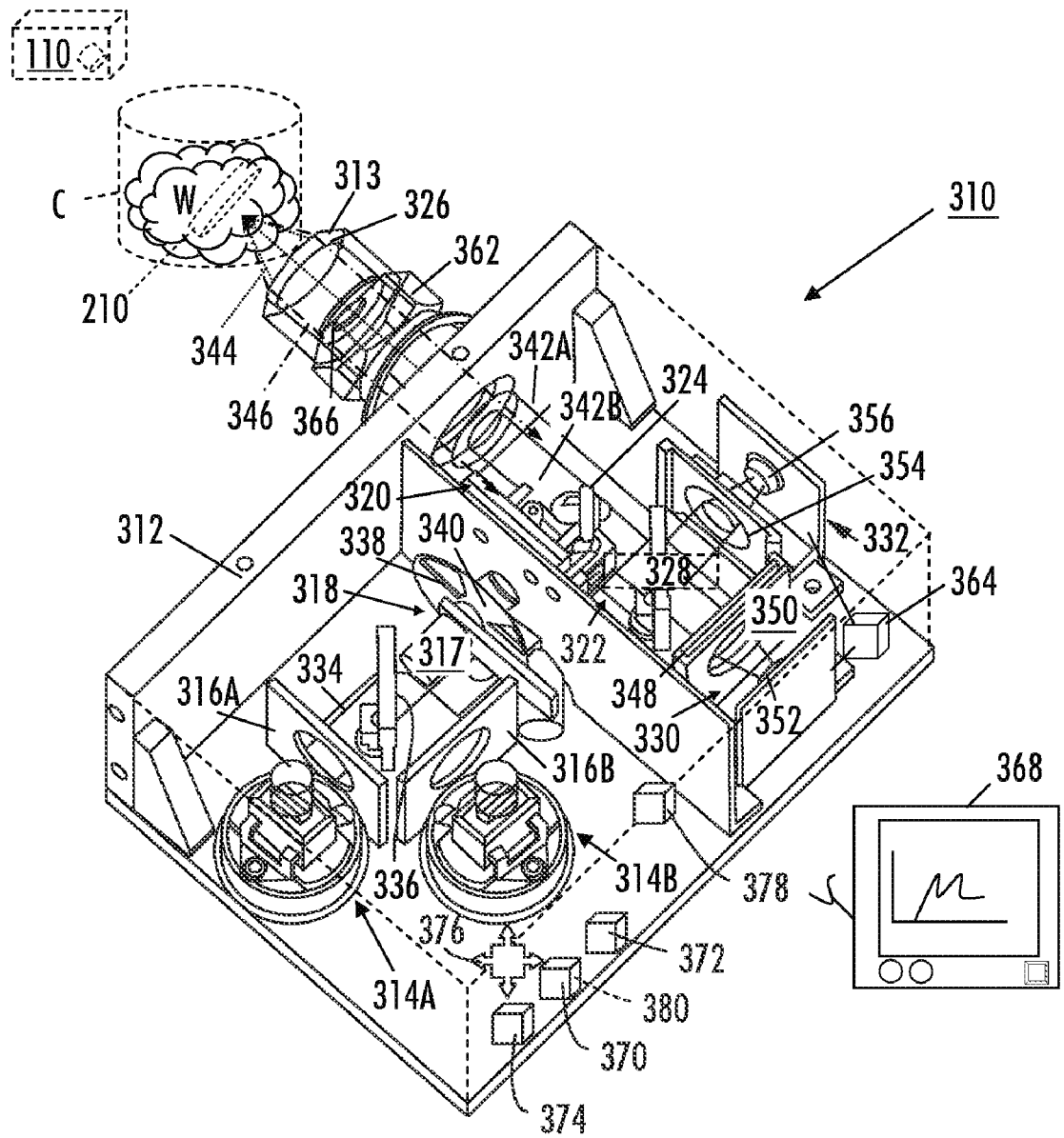
FIG. 6A is top perspective view of a wireless unit in accordance with a further aspect of the present disclosure.

With reference now to FIG. 6A, a third exemplary embodiment of the present subject matter, a wireless optical analysis and measurement system, is designated generally by reference number 310. Many aspects of the wireless optical analysis and measurement system 310 and its related components are similar to the foregoing embodiments; thus, for the sake of brevity, only certain differences are described below. To provide a full and enabling disclosure of the optical analysis system 310, however, when like or similar elements and components are not specifically described below; implicit reference is made to the foregoing descriptions.

Figure 7:
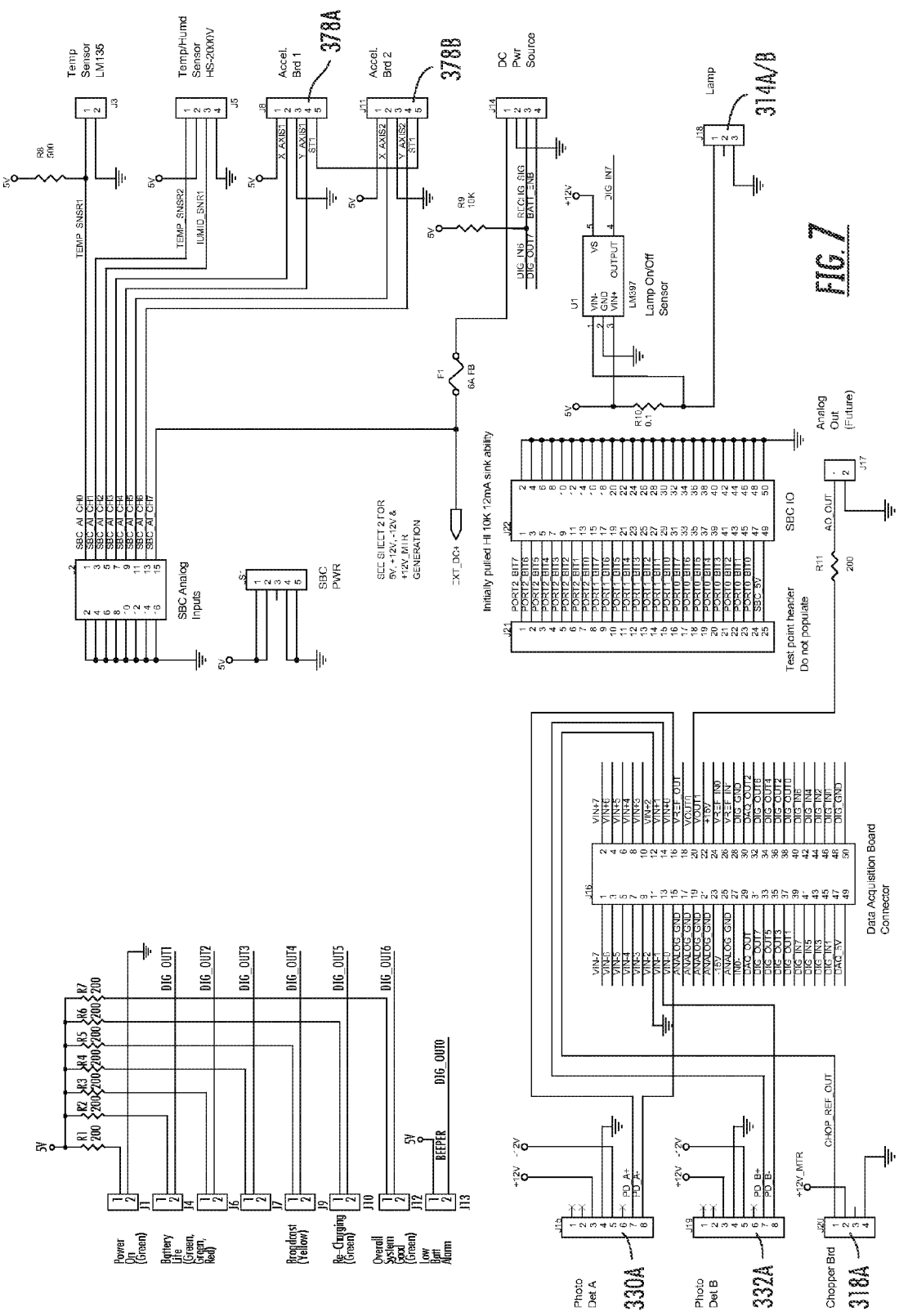
FIG. 7 is schematic diagram of the wireless unit as in FIG. 6A.
Figure 8:
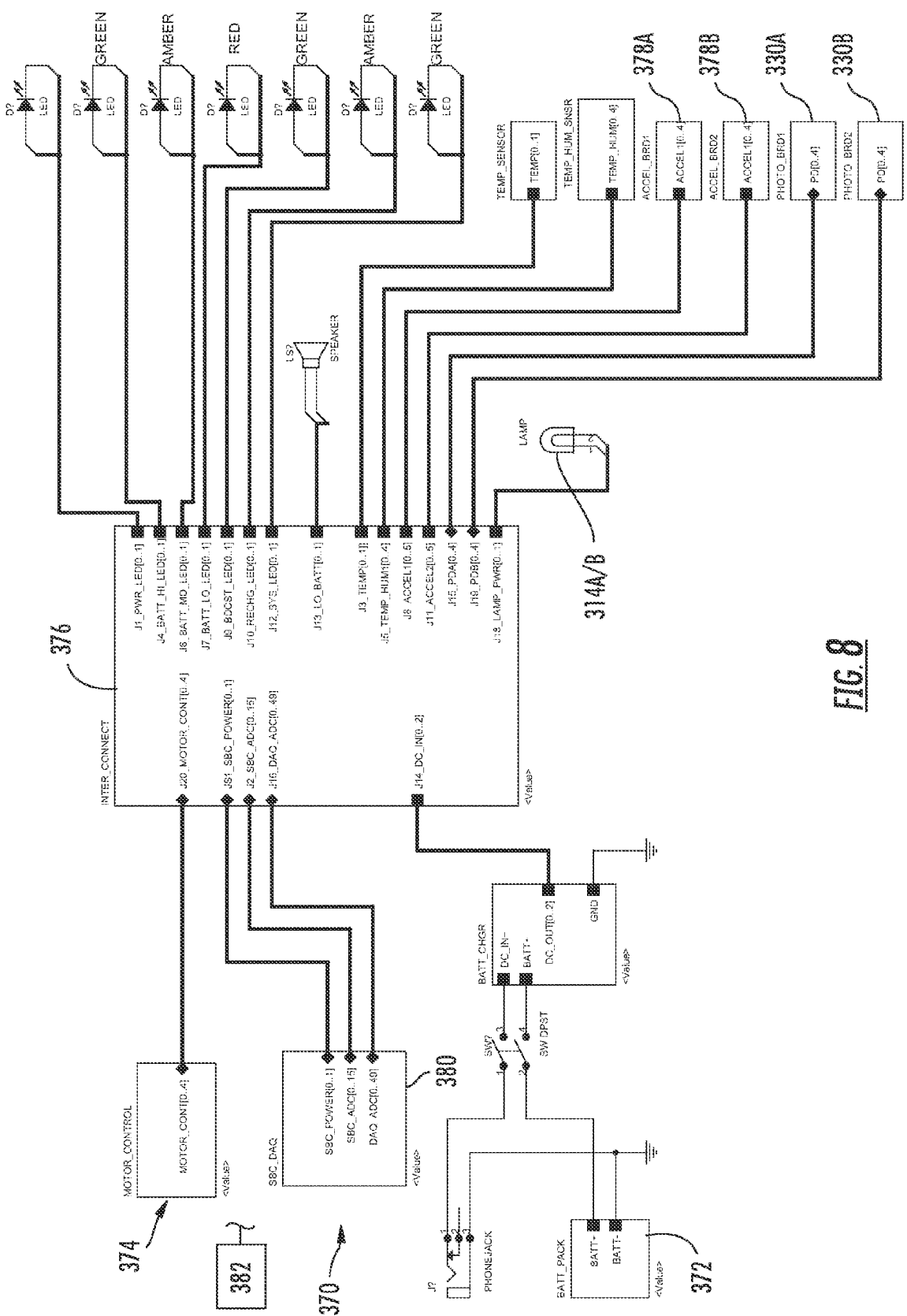
FIG. 8 is a schematic diagram of an interconnect board circuit of the wireless unit as in FIG. 6A.

As shown in FIGS. 6A, 7 and 8, the wireless optical analysis system 310 incorporates an optical computing system substantially as described above. More specifically, the wireless system 310 includes a housing 312, an illumination or light source 314, a chopper wheel 318 (and board 318A), one or more spectral elements 320, a focusing lens 326, a beam splitter 328, a first detector 330 (and board 330A) including a multivariate optical element 348, and a second detector 332 (and board 332A).

As its name implies, the wireless system 310 shown in FIGS. 6A, 7 and 8 is designed for remote operation. As shown, the wireless system 310 incorporates a signal and data processing computer 370, a rechargeable battery 372, and wireless control and communication 374 capabilities into a single unit. The wireless system 310 can be operated temporarily in a fully wireless mode using the included rechargeable battery 372, or in a powered mode for continuous operation. When operating in the powered mode, the battery 372 serves as an uninterruptible power supply. By way of example, the wireless system 310 can operate for 6 or more hours on the battery 372 between recharging.

As further shown in FIGS. 6A, 7 and 8, the battery 372 is connected to an interconnect board 376 with a relatively lower voltage threshold, which enables a greater range of usable voltage from the battery 372. Also shown, an orientation check-accelerometer 378 (and associated boards 378A, 378B) makes the wireless system 310 ideal in moving applications, such as for use with a pharmaceutical mixer or vessel C. The vessel C may be a rotating box having, for example, a 500 liter capacity (although larger or smaller capacities and geometries may be provided). In such a moving mixer C, material W is being tumbled inside the moving mixer C. As such, the material W being measured is not always in contact with an interrogation or measurement window (see, e.g., window 113 in FIG. 3). In such cases, the wireless system 310 should only measure the material W when the material W is in contact with the measurement window. Therefore, the accelerometer 378 serves to communicate position information to the computer 370 such that only system output from the period when the material W is in contact with the measurement window is used for concentration measurements. Alternatively, or additionally, the system may be programmed to sense when the material W is in contact with or proximate to the window and only take readings upon sensing such contact.

Figure 6B:
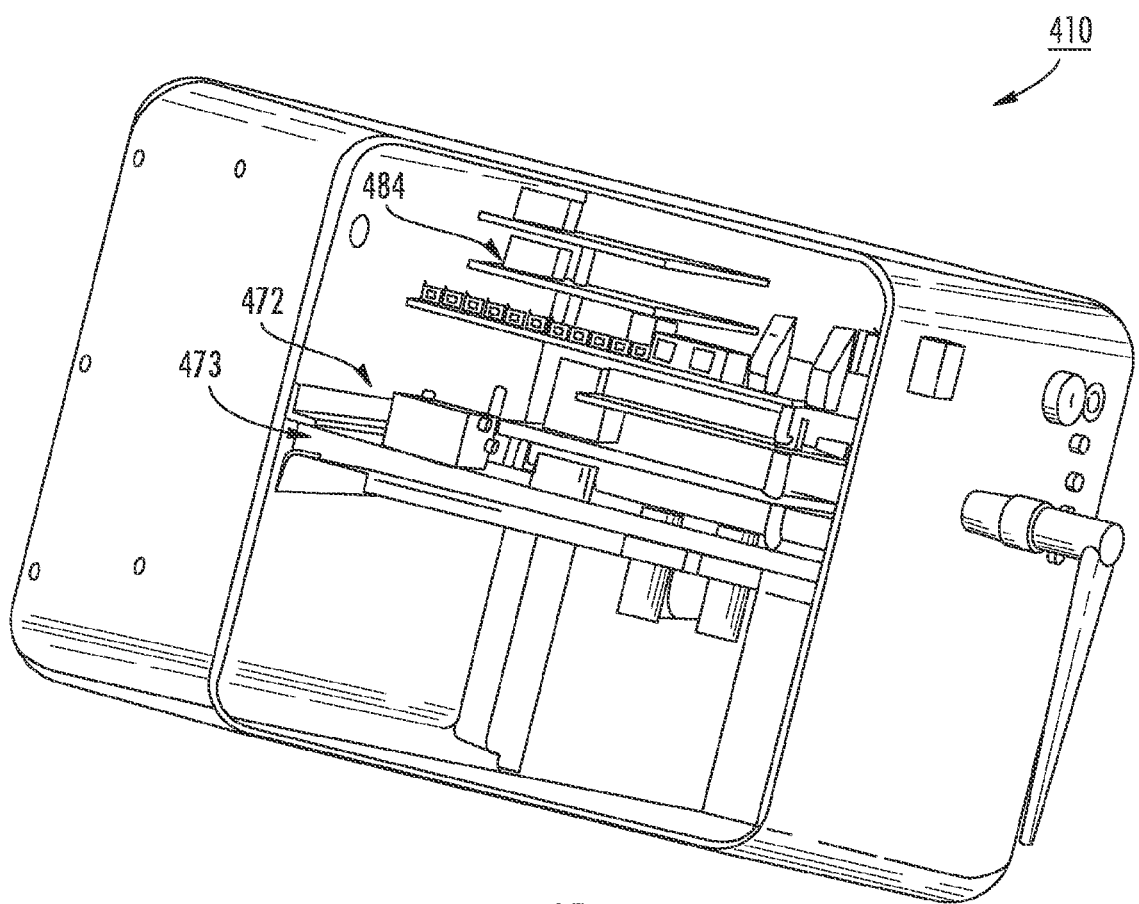
FIG. 6B is a perspective view of a wireless unit similar to FIG. 6A in accordance with a further aspect of the present disclosure.
Figure 6C:
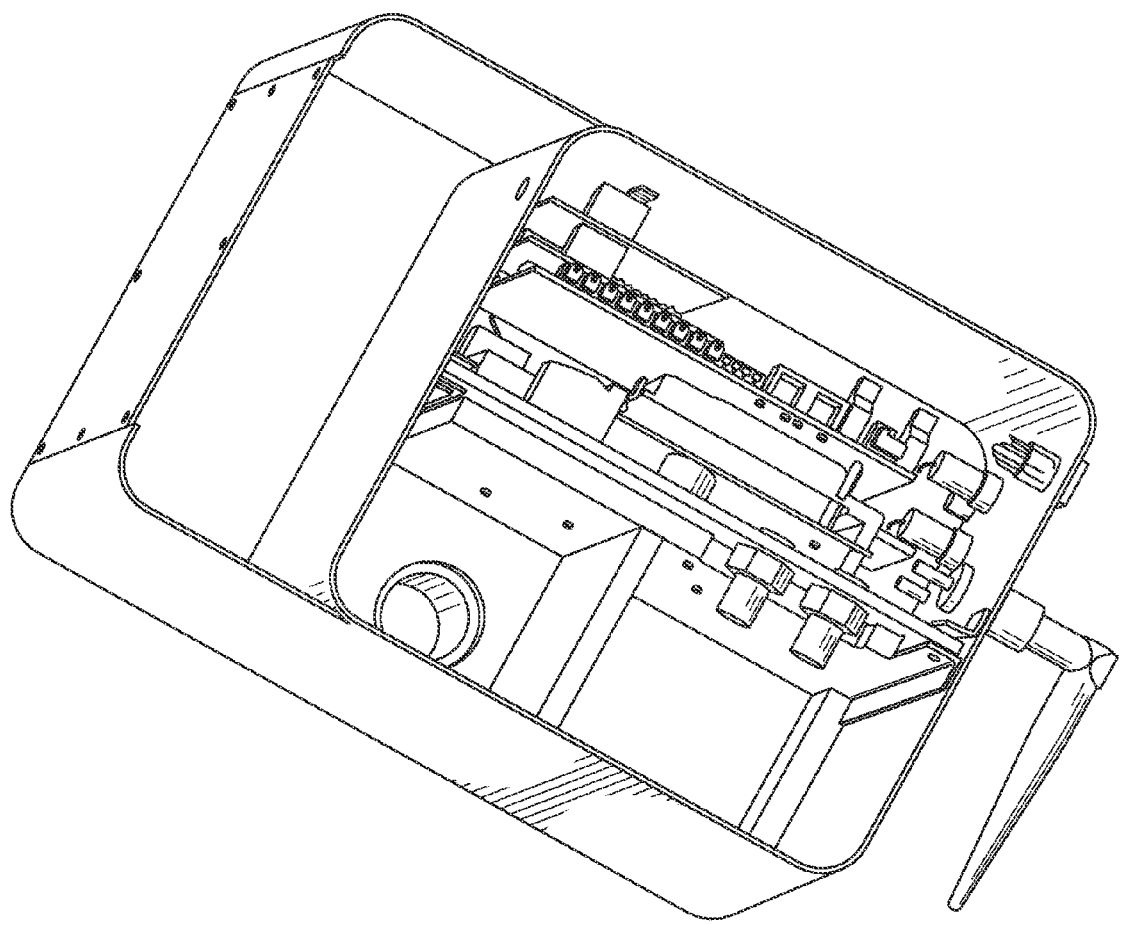
FIG. 6C is another perspective view of the wireless unit in FIG. 6B.

FIGS. 6B and 6C show another exemplary embodiment of the present subject matter, a wireless optical analysis and measurement system, which is designated generally by reference number 410. As shown, the wireless optical analysis and measurement system 410 includes a battery system 472 with a battery and a battery recharge board 473, an A/D converter 484, and an optical computer. Many aspects of the wireless optical analysis and measurement system 410 and its related components are similar to the foregoing embodiments. Therefore, reference is made to the foregoing descriptions to provide a full and enabling disclosure of the optical analysis system 410.

Turning now to FIG. 8 most clearly shows that the on-board computer 370 includes a data acquisition and conversion (DAQ) card 380, which inter alia enables the on-board computer 370 to sense moving mixers and collect compositional data therefrom. The on-board computer 370 is capable of signal processing and will have appropriate software loaded for a desired analyte analysis. As shown schematically, a central computer system 382 can be used to monitor and control several measurement systems including the wireless system 310. As known to those skilled in the art, the wireless system 310 can be programmed or controlled to send data to the central computer system 382 to provide data backup.

The skilled artisan will further appreciate that the disclosure is not limited to the foregoing exemplary arrangements. For example, the systems can be arranged with the mirrors and the detectors on an opposite side of the container C such that the light passes through the liquid sample into the mirror. Accordingly, in this alternatively arranged system, particle density in a fluid can be studied in conjunction with a chemical content of the fluid.

The disclosure may be better understood from the following tests and examples.

Example I

System I

A system similar to the optical analysis system 10 shown in the figures was constructed and used to make static measurements on aspirin/lactose.
System I Components:
Illumination: 20 W Gilway lamp
Spectral elements: 5 mm D2O, 5 mm Germanium
Optical window: none
Detector: PbS detector from New England Photoconductor
MOE: specific to test conditions.
Procedure and Results of Static Testing Using System I:
A powdered sample with a known composition was placed in a dish and the system light beam was focused on the powder. The output of the detectors was monitored and recorded. Aspirin/lactose samples covering the range of 100% aspirin to 100% lactose were tested.

Example II

System II

A system similar to the optical analysis system 10 shown in the figures was constructed and used to make dynamic measurements on aspirin/lactose.
System II Components:
Illumination: 20 W Gilway lamp
Spectral elements: 5 mm D2O, 5 mm Germanium
Optical window: sapphire window
Detector: PbS detector from New England Photoconductor
MOE: specific to test conditions.
Procedure and Results of Dynamic Testing Using System II:
The Aspirin/Lactose testing was made on a mixer bowl containing lactose and the system measured as aspirin was added to the system and mixed. Specifically, lactose powder was placed in the bowl of a mixer and the measurement system was attached the bowl using a Swagelok® brand fitting. A sapphire window was used to contain the powder in the bowl and allow the system to interrogate the powder. With the mixer turning, known amounts of aspirin were added and the system output signal was monitored and recorded. Aspirin was added in several allotments to about 37% final aspirin concentration.

Example III

System III

A system similar to the optical analysis system 10 shown in the figures was constructed and used to make static measurements on aspirin/lactose.
System III Components:
Illumination: 5 W Gilway lamp
Spectral elements: 5 mm D2O, 5 mm Germanium
Optical window: none
Detector: PbS detector from New England Photoconductor
MOE: specific to test conditions.
Procedure and Results of Dynamic Testing Using System III:
Similar to the examples above.

Although examples have been described in such a way as to provide an enabling disclosure for one skilled in the art to make and use the disclosure, it should be understood that the descriptive examples of the disclosure are not intended to limit the disclosure to use only as shown in the figures. For instance, the housing 16 can be shaped as a square, an oval, or in a variety of other shapes. Further, a variety of light sources can be substituted for those described above. It is intended to claim all such changes and modifications as fall within the scope of the appended claims and their equivalents. Thus, while exemplary embodiments of the disclosure have been shown and described, those skilled in the art will recognize that changes and modifications may be made to the foregoing examples without departing from the scope and spirit of the disclosure.

That which is claimed is:

1. An optical analysis system for measuring compositions, comprising:
   a light source being configured to radiate a first light;
   a modulator disposed in a ray path of the light, the modulator being configured to modulate the light to a desired frequency;
   a spectral element disposed proximate the modulator, the spectral element being configured to filter the light for a spectral range of interest of a sample;
   an optical filter mechanism disposed to receive a first light beam split from the light reflecting from the sample, the optical filter mechanism being configured to optically filter data carried by the first light beam into at least one orthogonal component of the first light beam;
   a first detector mechanism in communication with the optical filter mechanism to measure a property of the orthogonal component to measure the data carried by the first light beam;
   a second detector mechanism being configured to receive a second light beam split from the light reflecting from the sample for comparison of the property of the orthogonal component to the second light beam;
   an accelerometer being configured to sense when to acquire the data from the sample;
   a computer disposed in the system in communication with the first and second detector mechanisms for processing the data; and
   a battery system in electrical communication to provide stand-alone capability.

2. The optical analysis system as in claim 1, wherein the optical analysis system is operable in a transmission mode.

3. The optical analysis system as in claim 1, wherein the optical analysis system is operable in a reflectance mode.

4. The optical analysis system as in claim 1, wherein the modulator includes a plurality of windows, at least two of the windows having different materials to provide different spectral characteristics.

5. The optical analysis system as in claim 1, wherein the modulator includes a plurality of windows, at least window containing a multivariate optical element.

6. The optical analysis system as in claim 1, wherein the spectral element is a multivariate optical element selected for the sample based on components of the system.

7. The optical analysis system as in claim 1, wherein the computer includes a data acquisition and conversion card.

8. The optical analysis system as in claim 1, further comprising an interrogation window, the accelerometer being configured to sense when the sample is proximate the interrogation window, the accelerometer being in communication with the computer such that only when the sample is proximate the interrogation window is the data acquired from the sample.

9. The optical analysis system as in claim 1, further comprising an interrogation window, the accelerometer sensing when the system is in an orientation placing the sample proximate the interrogation window to acquire data from the sample.

10. The optical analysis system as in claim 1, further comprising an interrogation window, the accelerometer sensing when the sample is in the ray path of the light and being further configured to control data acquisition based thereon.

11. The optical analysis system as in claim 1, further comprising a beamsplitter being configured to split the light into the first beam and the second beam.

12. The optical analysis system as in claim 1, further comprising a cavity in communication with the spectral element, the cavity being configured to direct the light in a direction of the sample.

13. The optical analysis system as in claim 1, further comprising a conical mirror being configured to convert the light reflecting from the sample into the first light beam and the second light beam.

14. An optical analysis system utilizing a light source to radiate a light along a ray path, the optical analysis system comprising:
  a modulator disposed in a light ray path, the modulator being configured to modulate a light along the light ray path to a desired frequency;
  a spectral element disposed proximate the modulator, the spectral element being configured to filter the light for a spectral range of interest of a sample;
  a conical mirror being configured to convert the light reflecting from the sample into a directed light;
  a beamsplitter being configured to split the directed light into a first beam and a second beam;
  an optical filter mechanism disposed to receive the first beam, the optical filter mechanism being configured to optically filter data carried by the first beam into at least one orthogonal component of the first beam;
  a first detector mechanism in communication with the optical filter mechanism to measure a property of the orthogonal component to measure the data;
  a second detector mechanism being configured to receive the second beam for comparison of the property of the orthogonal component to the second beam;
  an accelerometer being configured to control the data acquisition such that only detector signals during the period of time when a material sample is in proximity to the interrogation window are used for calculation;
  a computer having a data acquisition and conversion card, the computer disposed in the system in communication with the first and second detector mechanisms for signal processing; and
  a wireless system in communication with the computer to provide stand-alone operation capability.

15. The optical analysis system as in claim 14, wherein the optical analysis system is operable in one of a transmission mode and a reflectance mode.

16. The optical analysis system as in claim 14, wherein the wireless system is a battery and charging system disposed in the optical analysis system.

17. The optical analysis system as in claim 14, further comprising a cavity in communication with the spectral element, the cavity being configured to direct the light in a direction of the sample.

18. A method of determining information carried by light, comprising:
  filtering a light through a spectral element for a spectral range of interest of a sample;
  focusing the filtered light through an interrogation window proximate the sample when the sample is in proximity to the interrogation window;
  reflecting the light from the sample in a direction of a beamsplitter, the light being reflected from the sample carrying data from the sample;
  splitting the data-carrying light with the beamsplitter into a first light and a second light;
  optically filtering the data of the first light with a multivariate optical element into an orthogonal component;
  directing the first light filtered by the multivariate optical element onto a first photodetector;
  directing the second light onto a second photodetector;
  comparing the orthogonal component to information present in the second light to determine a property of the sample; and
  using an accelerometer to sense a system orientation placing the sample proximate the interrogation window to acquire data from the sample.

19. The method as in claim 18, wherein the light has a focal point in the sample.

20. The method as in claim 18, wherein wirelessly transmitting is accomplished utilizing a stand-alone computer disposed in the optical analysis system.

21. The method as in claim 18, further comprising loading software in the stand-alone computer for a desired analyte analysis.

22. A method of determining information carried by light, comprising:
  filtering a light through a spectral element for a spectral range of interest of a sample;
  focusing the filtered light through an interrogation window proximate the sample when the sample is in proximity to the interrogation window;
  reflecting the light from the sample in a direction of a beamsplitter, the light being reflected from the sample carrying data from the sample;
  splitting the data-carrying light with the beamsplitter into a first light and a second light;
  optically filtering the data of the first light with a multivariate optical element into an orthogonal component;
  directing the first light filtered by the multivariate optical element onto a first photodetector;

directing the second light onto a second photodetector;

comparing the orthogonal component to information present in the second light to determine a property of the sample; and wirelessly transmitting the property of the sample, wherein wirelessly transmitting is accomplished using a battery and charging system disposed in the optical analysis system.

23. The method of claim 18, wherein the material sample is a hydrocarbon, the method further comprising analyzing the components of the hydrocarbon.

24. An optical analysis system for measuring compositions, comprising:

a light source being configured to radiate a first light;

a modulator disposed in a ray path of the light, the modulator being configured to modulate the light to a desired frequency;

a spectral element disposed proximate the modulator, the spectral element being configured to filter the light for a spectral range of interest of a sample;

an optical filter mechanism disposed to receive a first light beam split from the light reflecting from the sample, the optical filter mechanism being configured to optically filter data carried by the first light beam into at least one orthogonal component of the first light beam;

a first detector mechanism in communication with the optical filter mechanism to measure a property of the orthogonal component;

a second detector mechanism being configured to receive a second light beam split from the light reflecting from the sample for comparison of the property of the orthogonal component to the second light beam; and an accelerometer being configured to sense when to acquire the data from the sample.

25. The optical analysis system as in claim 24, wherein the spectral element is a multivariate optical element.

26. The optical analysis system as in claim 24, further comprising a computer disposed in the system in communication with the first and second detector mechanisms for processing the data; and an interrogation window, the accelerometer being configured to sense when the sample is proximate the interrogation window, the accelerometer being in communication with the computer such that only when the sample is proximate the interrogation window is the data acquired from the sample.

27. The optical analysis system as in claim 24, further comprising an interrogation window, the accelerometer sensing when the system is in an orientation placing the sample proximate the interrogation window to acquire data from the sample.

28. The optical analysis system as in claim 24, further comprising an interrogation window, the accelerometer sensing when the sample is in the ray path of the light and being further configured to control data acquisition based thereon.

* * * * *